United States Patent [19]
Röhrscheid

[11] Patent Number: 4,987,238
[45] Date of Patent: Jan. 22, 1991

[54] PROCESS FOR THE PREPARATION OF HIGH-PURITY 5,5'-[2,2,2-TRIFLUORO-1-(TRIFLUOROME-THYL)-ETHYLIDENE]BIS-1,3-ISOBEN-ZOFURANDIONE

[75] Inventor: Freimund Röhrscheid, Kelkheim, Fed. Rep. of Germany

[73] Assignee: Hoechst Aktiengesellschaft, Frankfurt am Main, Fed. Rep. of Germany

[21] Appl. No.: 395,971

[22] Filed: Aug. 2, 1989

[30] Foreign Application Priority Data

Aug. 4, 1988 [DE] Fed. Rep. of Germany ....... 3826572

[51] Int. Cl.$^5$ .......................................... C07D 261/20
[52] U.S. Cl. ..................................... 549/241; 562/488
[58] Field of Search .......................... 549/241; 562/488

[56] References Cited

U.S. PATENT DOCUMENTS 3,310,573  3/1967  Coe ...................................... 549/241
4,906,760  3/1990  Mueller et al. ....................... 549/241

OTHER PUBLICATIONS

Chemical Abstract, vol. 100, #91886r, Grabchak et al., "Equilibrium Exchange of Ions on Activated Carbons", 1984.
Chemical Abstract, vol. 104, #149653p, Sei et al, "Purification of Aromatic Polyesters", 1985.
Chemical Abstract, vol. 96, #205,865q, Groshkov, "Ways of Increasing the Efficiency of Ion Exchange Methods for Mixture Separation and Substance Purification", 1982.
Chemical Abstract, vol. 105, #8461h, Szolcsanyi et al., "Prospective Principle of Separation of Chemical Components", 1986.

Primary Examiner—Richard L. Raymond
Assistant Examiner—Raymond Covington

[57] ABSTRACT

A process for the preparation of high-purity perfluorinated compounds, specifically of an aromatic tetracarboxylic acid and its anhydride, 5,5'-[2,2,2-trifluoro-1-(trifluoromethyl)-ethylidene]bis-1,3-isobenzofurandione, by a multi-step treatment of the crude compounds. The metal ion content of the compounds treated is reduced considerably. After polymerization with an aromatic diamine, the anhydride is used in microelectronics.

14 Claims, No Drawings

PROCESS FOR THE PREPARATION OF HIGH-PURITY 5,5'-[2,2,2-TRIFLUORO-1-(TRIFLUOROMETHYL)-ETHYLIDENE]BIS-1,3-ISOBENZOFURANDIONE

DESCRIPTION

The invention relates to a process for the preparation of high-purity perfluorinated compounds, specifically of an aromatic tetracarboxylic acid and its anhydride, by a multi-step treatment of the crude compounds. The metal ion content of the compounds treated is reduced considerably. After polymerization with an aromatic diamine, the anhydride is used in microelectronics. 5,5'-[2,2,2-trifluoro-1-(trifluoromethyl)-ethylidene]bis-1,3-isobenzofurandione, also known as 2,2-bis(3,4-dicarboxyphenyl)hexafluoropropane dianhydride, hereinafter called 6F dianhydride or, in short, "6F-DA", is mainly used for the polycondensation with aromatic diamines to give polyimides. These polyimides are in particular suitable for technologically demanding purposes, for example for coatings in airplane construction which can be subjected to high thermal stress or, due to their very low dielectric constants, in microelectronics. This optimum range of properties of the polyimides which contain trifluoromethyl groups can, however, only be achieved by using high-purity 6F dianhydride.

This means that, if 6F dianhydride is contaminated by compounds such as

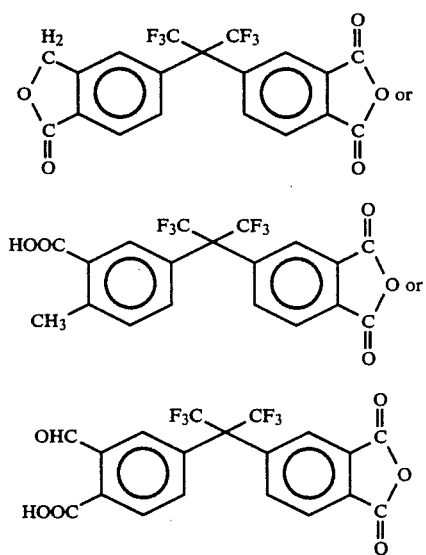

which originate from the preparation process, the result is either termination of the polycondensation reaction or formation of a weak link in the polyimide chain, which reduces the mechanical strength and the thermal stability. If used in microelectronics, an additional requirement is that the 6F dianhydride used has a very low metal content (Fe, Co, Mn, Ni, Na etc.) of at most 1 ppm.

The object was therefore to provide high-purity 6F dianhydride which can be polymerized with aromatic diamines and used as polyimide preferably in microelectronics.

Dixylylhexafluoropropane (DX-F6) and its oxidation with potassium permanganate in a mixture of pyridine and water to give the potassium salt of 2,2-bis(3,4-dicarboxyphenyl)hexafluoropropane (6F tetracarboxylic acid) and the preparation of the corresponding 6F dianhydride is described in US-A 3,310,573. The oxidation procedure has a high demand of chemicals, the isolation of the tetracarboxylic acid is very complicated, and the solvent system used and the manganese oxide have to be worked up. The purification of the 6F dianhydride is carried out by simple sublimation. Nothing is mentioned about the degree of purity.

The object is achieved by a multi-step process in which impure 6F tetracarboxylic acid, such as is formed, for example, by oxidation of dixylylhexafluoropropane by one of the known procedures using $KMnO_4$, nitric acid or air oxygen, is freed of impurities in several steps, the steps being effective for the entire range of the different types of impurities only when combined.

The invention accordingly relates to a process for the preparation of high-purity 5,5'-[2,2,2-trifluoro-1-(trifluoromethyl)-ethylidene]bis-1,3-isobenzofurandione (6F dianhydride=6F-DA) in which a concentrated solution of 6F tetracarboxylic acid in water or in dilute acetic acid is subjected to the following steps:

(a) treatment of the solution with adsorbents and/or filtering aids, followed by filtration,
(b) treatment of filtrate (a) with ion-exchanger,
(c) cooling of the solution treated according to (b) to form pure 6F tetracarboxylic acid,
(d) filtration of 6F tetracarboxylic acid, and
(e) conversion of 6F tetracarboxylic acid to 6F dianhydride, as a result of which the compound obtained has a purity of $\geq 99.5\%$ at a total metal ion content of $\leq 1$ ppm. These process steps (a) to (e) each have a further specific design and are described below in more detail.

According to a still unpublished, particularly favorable procedure (German Patent Application P No. 3,739,800.8), dixylylhexafluoropropane is oxidized in the presence of Co, Mn, Ce and Br ions in glacial acetic acid with air oxygen to give 6F tetracarboxylic acid. After the addition of acetic anhydride to the oxidized and dehydrated reaction solution, 6F dianhydride crystallizes and is present, after washing and drying, in a yield of 96% and a purity of 94–96%, which, however, is not sufficient for the abovementioned purposes.

Direct isolation of 6F tetracarboxylic acid from the reaction solution is not possible, because it often crystallizes only after days and then only incompletely in a form which is difficult to filter.

To obtain a concentrated solution of 6F tetracarboxylic acid in water or in acetic acid/water mixtures, (1) the concentration can be started directly with the oxidation solution, as described above, or, alternatively, (2) the route via the 6F dianhydride, which is hydrolyzed, can be chosen.

(1) The oxidation solution is evaporated up to a boiler temperature of 130°–160° C., preferably 140°–150° C., particularly preferably 145° C., and then water is metered in under an inert gas pressure of about 6 bar at 135°–140° C. until the acetic acid concentration is 2–30, preferably 5–20, in particular 8–12, % by weight. In this procedure, it was surprising that no crystallization, as with other polycarboxylic acids, occurred upon evaporation of the reaction solution and that instead a stirrable melt having a low acetic acid content was present at a boiler temperature of 145° C.

(2) 6F dianhydride can be hydrolyzed by means of boiling water only very slowly over a period of days.

Surprisingly, it has been found that the hydrolysis of 6F dianhydride is completed in less than half an hour, if acetic acid in the amounts mentioned above is added to the water. It is particularly advantageous to use 7 to 8% of acetic acid.

The solution of 6F tetracarboxylic acid in dilute aqueous acetic acid has a cloudiness which consists of very finely divided iron salt of the 6F tetracarboxylic acid and is not retained by finely porous filters. By adding adsorbents and/or filtering aids in process step (a), such as activated carbon, kieselguhr or by a combination of activated carbon and kieselguhr, this cloudiness is adsorbed and can be filtered off. The amount added depends on the degree of contamination. In general, the addition of 2 to 10 g per liter of solution is sufficient. In step (b), clear solution (a) is passed through a strongly acidic ion-exchanger which preferably consists of a polystyrenesulfonic acid. It is also preferred to carry out this treatment at elevated temperature, for example at 70 to 90° C. This removes the metal ions almost quantitatively. Surprisingly, the yield of 6F tetracarboxylic acid also increases by an amount which corresponds to the equivalent amount of the metal ions.

The 6F tetracarboxylic acid crystallizes by cooling solution (b) to 10 to 25° C., preferably to 18°-22° C.. The leaflet-like crystals are filtered and washed with water or dilute aqueous acetic acid. The filtrate contains mainly those carboxylic acids which do not crystallize even after evaporation. The filtration proceeds very slowly in many cases. The filtration time can surprisingly be shortened by carrying out the crystallization from dilute aqueous acetic acid preferably containing 8 to 12% of acetic acid in water. A shortening of the filtration time can also be achieved by adding, relative to the aqueous solvent, 0.1 to 2, preferably 0.2 to 0.6, % by weight of an inert hydrocarbon, preferably toluene, ethylbenzene or the various xylenes.

The filter cake which consists of 6F tetracarboxylic acid and has a total metal ion content of $\leq 1$ ppm can be dried and dehydrated by heating under reduced pressure to 175 to 220° C., preferably 180°-190° C., to give the 6F dianhydride.

It is possible to improve the purity of the 6F dianhydride further, that is to $\geq 99.5\%$, by carrying out the formation of the 6F dianhydride in a hydrocarbon, preferably in an aromatic hydrocarbon. A particularly simple procedure consists in suspending the water-moist filter cake of 6F tetracarboxylic acid in an inert hydrocarbon and distilling off the water azeotropically. The suspension thus formed consisting of anhydrous 6F tetracarboxylic acid can be converted to the 6F dianhydride in two ways.

(a) Thermally. By heating the dicarboxylic acid to more than 140° C., the anhydride ring is formed by elimination of water. Rapid formation of the anhydride is preferably carried out above 170° C., particularly preferably at 180°-220° C. Suitable solvents are those having a high boiling point, such as diphenyl ether or tetrahydronaphthalene, or, if desired, lower-boiling solvents such as toluene or o-xylene are used at 180°-220° C. under inert gas pressure. As soon as no more water distils over, the solution is allowed to cool with stirring.

(b) Chemically. Acetic anhydride is added to the anhydrous suspension of 6F tetracarboxylic acid in the hydrocarbon in such an amount that it is present in excess, preferably 0.5-25 mol % of acetic anhydride, relative to the theoretically possible yield of 6F dianhydride. The 6F dianhydride forms beautiful heavy crystals, some of which crystallize only upon cooling. Impurities, for example those having the formula

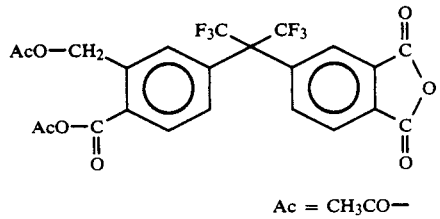

Ac = CH$_3$CO— remain in solution. After they have been filtered off with suction, the crystals are washed with a hydrocarbon and dried. For the chemical formation of 6F dianhydride, preferably aromatic hydrocarbons having a medium boiling range of 110°-150° C., for example toluene, ethylbenzene and the various xylenes, are used. Using these hydrocarbons, it is possible to obtain a sufficiently high reaction temperature and, on the other hand, their boiling points are still low enough for them to be easily removed by simple drying under reduced pressure from the 6F dianhydride crystals which have been filtered off with suction.

EXAMPLE

1. Preparation of a solution of 6F tetracarboxylic acid 2,2-bis(3,4-dicarboxyphenyl)hexafluoropropane (6F tetracarboxylic acid)

In a 1 l glass autoclave equipped with dosing pump, thermometer, stirrer and reflux condenser, a solution of 2.5 g of cobalt acetate tetrahydrate, 2.45 g of manganese acetate tetrahydrate and 0.44 g of hydrogen bromide in 310 ml of glacial acetic acid were initially introduced. Parallel to this solution, a solution of 180.2 g of dixylyl-hexafluoropropane (DX-6F) in a mixture of 102 g of acetic anhydride and 60 g of glacial acetic acid was kept ready for use in a metering device. The autoclave was put under a total pressure of 7.5 bar by passing in oxygen, an effluent gas value of 30 Nl/h was established, and the contents were heated.

At about 160° C., the metering-in of dixylylhexafluoropropane was started, and the total amount was added within 100 minutes. The temperature of the exothermic reaction was maintained at 170°-175° C., and the batch was maintained at 175° C. by heating for another hour, after the metering had been completed. About 500 g of the acetic acid/water mixture were distilled off at atmospheric pressure from the reaction mixture (about 790 to 800 g). As soon as the temperature of the residue had increased to 145° C., the autoclave was put under a pressure of 4 bar by passing in nitrogen, 500 g of distilled water were added, and the mixture was maintained at 145° C. for an hour. It was then cooled to about 90° C., and the solution was then removed.

2. Clearing and filtering (step a)

A suspension of 4 g of kieselguhr in 12 g of water was added to the hot solution (90° C.), which had a slight cloudiness. The mixture was stirred at 90° C. for 15 minutes and filtered through a suction filter while hot. The first 100 ml of the filtrate were poured back and filtered again.

3. Removal of the metal ions (step b) The clear filtrate (about 800 g 675 ml) having an acetic acid content of 8% was poured into a heatable raised 1 l vessel and heated to 80° C. From this vessel, the solution was added to a heated perpendicular exchanger column (length 100 cm, diameter 2 cm) of 80° C., which was filled to a height of 80 cm with freshly activated, strongly acidic ion-exchanger (polystyrenesulfonic acid, 2.1 mol/1 Lewatit S 100 from Bayer AG, Leverkusen). Passage time 2 hours. Finally, 100 ml of water were run through the column. 775 g of eluate, metal ion content: <1 mg of Co, Mn per liter of solution.

4. Crystallization and washing of the 6F tetracarboxylic acid (steps c and d)

The crystallization was carried out in a cylindrical vessel equipped with an anchor stirrer. 3 ml of o-xylene were added to the hot eluate (775 ml). The mixture was cooled to 21° C. The resulting thick paste of crystal leaflets was filtered off with suction. The filter cake was washed by the addition of 12 times 25 ml each of distilled water and finally sucked dry for about 30 minutes. Yield: 400 g of water-moist product.

5. Formation of the 6F dianhydride (step e)

The water-moist 6F tetracarboxylic acid (400 g) was suspended in a flask equipped with stirrer and water separator in 450 ml of o-xylene. The batch was heated with vigorous stirring, and about 180 g of water were distilled off. At the end, the internal temperature increased to 142° C., and only o-xylene distilled off. A crystal suspension of anhydrous 6F tetracarboxylic acid remained in the flask. Acetic anhydride (118.8 g) was added dropwise to the boiling suspension over a period of 2 hours. Heating under reflux was then continued for another 3 hours. The concentration of acetic anhydride at the end was about 4.5%. The suspension was cooled to 30° C. with stirring over a period of 3 hours, then filtered off with suction, and the product was washed four times with 35 ml each of o-xylene. After the last washing, the product was thoroughly filtered off with suction. The first filtrates were yellow and the last one colorless. The nicely crystalline filter cake was dried at 100° C. and 65 mbar for 6 hours.

Yield: 195 g (about 88% of theory, relative to DX-F6)

M.p.: 244°-245° C.
Purity: 99.9%
Metal content: 0.5 ppm (sum of all metal ions)

I claim:

1. A process for the preparation of high-purity 5,5'-[2,2,2-trifluoro-1-(trifluoromethyl)-ethylene]bis-1,3-isobenzofurandione (6F dianhydride=6F-DA), which comprises subjecting a concentrated solution of 6F tetracarboxylic acid in water or in dilute acetic acid to the following steps:
    (a) treatment of the solution with adsorbents and/or filtering aids, followed by filtration,
    (b) treatment of filtrate resulting from step (a) with ion-exchanger,
    (c) cooling of the solution treated according to step (b) to form pure 6F tetracarboxylic acid,
    (d) filtration of 6F tetracarboxylic acid and
    (e) conversion of 6F tetracarboxylic acid to 6F dianhydride, and recovery of 6F dianhydride having a purity of $\geq 99.5\%$ at a total metal ion content of $\leq 1$ ppm.

2. The process as claimed in claim 1, wherein the concentrated solution used is a reaction solution of the preparation of 6F tetracarboxylic acid or a hydrolysis product of 6F-DA.

3. The process as claimed in claim 1, wherein the concentrated solution has an acetic acid concentration of 2 to 30% by weight.

4. The process as claimed in claim 1, wherein in step (a) activated carbon, kieselguhr or a mixture of both are used.

5. The process as claimed in claim 1, wherein colloidal metal salts are removed in step (a).

6. The process as claimed in claim 1, wherein in step (b) a strongly acidic ion-exchanger is used.

7. The process as claimed in claim 6, wherein the ion-exchanger used is polystyrenesulfonic acid.

8. The process as claimed in claim 1, wherein the treatment in step (b) is carried out at elevated temperature.

9. The process as claimed in claim 8, wherein the temperature in step (b) is 70°-90° C.

10. The process as claimed in claim 1, wherein the temperature of the solution obtained from step (b) is reduced to 10 to 25° C. in step (c).

11. The process as claimed in claim 10, wherein, before the solution is cooled, 0.1 to 2% by weight, relative to the aqueous solvent, of an inert hydrocarbon is added with stirring.

12. The process as claimed in claim 11, wherein toluene, ethylbenzene or various xylenes are used as the inert hydrocarbon.

13. The process as claimed in claim 1, wherein (e) the formation of 6F-DA from the purified 6F tetracarboxylic acid is carried out by the one of the steps:
    (e1) heating the dried filter cake of the acid under reduced pressure to 175 - 220° C.,
    (e2) heating an anhydrous suspension of the acid in an inert solvent at a temperature above 140° C. if appropriate under inert gas pressure, or
    (e3) reacting an anhydrous suspension of the acid in an inert solvent with acetic anhydride, the crystals obtained in processes (e2) and (e3) being washed with a hydrocarbon and subsequently dried.

14. The process as claimed in claim 13, wherein in step
    (e2) diphenyl ether, tetrahydronaphthalene, toluene or o-xylene are used as the solvent.

* * * * *

UNITED STATES PATENT AND TRADEMARK OFFICE
CERTIFICATE OF CORRECTION

PATENT NO. : 4,987,238
DATED : 01/22/91
INVENTOR(S) : Freimund Rohrscheid

It is certified that error appears in the above-identified patent and that said Letters Patent is hereby corrected as shown below:

At column 4, line 67, insert -- $\hat{=}$ -- between "800g" and "675 ml".

In claim 1, column 5, line 47, "(trifluoromethyl)-ethylene" should read -- (trifluoromethyl)-ethylidene -- .

In claim 13, column 6, line 41 "by the one" should read -- by one -- .

Signed and Sealed this

Eleventh Day of August, 1992

*Attest:*

DOUGLAS B. COMER

*Attesting Officer*     *Acting Commissioner of Patents and Trademarks*